United States Patent [19]
Britton et al.

[11] Patent Number: 5,863,553
[45] Date of Patent: Jan. 26, 1999

[54] BIOERODIBLE CONTRACEPTIVE SUPPOSITORY

[75] Inventors: Peter Britton, Scotch Plains, N.J.; Patricia Flanagan, Naperville, Ill.; William P. Hart, Freehold, N.J.; Deborah Linkin, Madeira Beach, Fla.

[73] Assignee: McNeil-PPC, Inc., Skillman, N.J.

[21] Appl. No.: 813,526

[22] Filed: Mar. 7, 1997

Related U.S. Application Data

[63] Continuation of Ser. No. 644,437, May 13, 1996, abandoned, which is a continuation of Ser. No. 252,504, Jun. 1, 1994, abandoned, which is a division of Ser. No. 943,258, Sep. 10, 1992, Pat. No. 5,354,558.

[51] Int. Cl.$^6$ ...................................................... A61K 9/02
[52] U.S. Cl. .................. 424/433; 424/430; 424/DIG. 14; 424/DIG. 15; 514/841; 514/843; 514/945; 514/967; 514/774; 514/777

[58] Field of Search ...................................... 424/433, 430, 424/DIG. 14, DIG. 15; 514/843, 945, 967

[56] References Cited

U.S. PATENT DOCUMENTS 4,707,362  11/1987  Nuwayser ................................ 424/433

*Primary Examiner*—Thurman K. Page
*Assistant Examiner*—James M. Spear

[57] ABSTRACT

The invention relates to an intravaginally-dissolvable contraceptive suppository, a method of using said suppository, and an improved method of manufacturing said birth control device. The suppositories of the invention, which comprise a lyophilized foam and a contraceptive, have a dissolution time of at least about 2 hours, and up to about 24 hours, and provide superior protection against pregnancy.

4 Claims, No Drawings

BIOERODIBLE CONTRACEPTIVE SUPPOSITORY

This is a continuation of application Ser. No. 08/644,437, filed May 13, 1996, abandoned which is a continuation of Ser. No. 08/252,504, filed Jun. 1, 1994, abandoned which is a division of application Ser. No. 07/943,253, filed Sept. 10, 1992, U.S. Pat. No. 5,354,558 all of which are hereby incorporated by reference.

BACKGROUND OF THE INVENTION

The invention relates to a bioerodible contraceptive device, and, more particularly, to an intravaginally-dissolvable contraceptive suppository comprising a lyophilized foam and a contraceptive, a method of using such suppositories and a method for manufacturing them.

Vaginal contraceptives are well-known in the art, including, for example, spermicidal creams and gels. These products can be used alone or in conjunction with removable contraceptive devices, such as intrauterine devices. Although many of these products are readily available without a prescription, there are several disadvantages associated with their use. The effectiveness of these products is generally limited to one or two hours. In addition, these creams or gels tend to melt very readily and, thus, are easily discharged from the vagina, thereby further limiting their effectiveness. Furthermore, the tendency to rapidly melt makes such products inconvenient and messy to use.

In the area of foams, although the use of foams and freeze-dried foams to deliver various active ingredients is well-known, such foams generally do not possess the requisite characteristics that would render them suitable for use as a contraceptive suppository. For example, in U.S. Pat. No. 4,642,903, Davies discloses the use of freeze-dried foams for dispensing a variety of active ingredients. However, Davis' foams are designed to have very rapid dissolution rates (virtually instantaneous) which would render his foam highly ineffective for use as a contraceptive. Moreover, it is not possible to control the degree of aeration in Davis' foaming process; accordingly, using Davis' method it is not possible to control densities, dosage delivery rates and dissolution times of the foams which is critical to the manufacture of a contraceptive suppository.

Similarly, in U.S. Pat. No. 4,292,972, Pawelchak et al. discloses a lyophilized foam sponge product containing sodium carboxymethylcellulose, pectin, gelatin and a pharmaceutical, that is intended primarily for use as a hemostatic agent. Unfortunately, Pawelchak's dispersions do not aerate readily; therefore, Pawelchak's freeze-dried foams possess poor structural integrity and dissolve too quickly.

Accordingly, a need exists for a bioerodible vaginal contraceptive suppository that, provides for the sustained and/or controlled release of a contraceptive, gives effective protection against pregnancy for at least several hours, and which is not readily expelled. In addition, there is a need for a method of manufacturing such suppositories whereby the dissolution time and the drug delivery rate of the suppository can be substantially controlled and readily reproduced.

SUMMARY OF THE INVENTION

It has been found that an intravaginally dissolvable contraceptive suppository comprising, a water-soluble lyophilized foam and a contraceptive. The suppository, having a density of about 0.001 to about 0.1 gm/cc and a dissolution time of at least about 2 hours, can provide for the sustained and controlled release of a contraceptive for at least 2 hours. The suppositories have dissolution times of at least about 2 hours to about 24 hours, and therefore, are very slow to dissolve. In addition, upon dissolution, the suppositories form viscous gels which maintain good structural integrity intravaginally. Therefore, the user does not experience messy discharge and premature expulsion of the device. To further facilitate retention and promote effectiveness, the suppositories incorporate foams that render them mucoadherent.

Accordingly, the suppositories of the invention are comprised of foams that possess characteristics that render them ideal for incorporation into a contraceptive suppository. Unlike the suppository devices of the prior art which are ineffectual after a couple of hours, the devices of the invention provide effective intravaginal contraception to the user for a prolonged period following intercourse.

In addition, the disadvantages associated with prior methods of manufacture for active-ingredient-dispensing foams are overcome in the present invention. It has been determined that by using a continuous, enclosed mixer that is capable of operating under pressure to foam a liquid dispersion, it is possible to regulate certain foaming parameters and thereby control the liquid density of the foamed dispersions prior to lyophilization. The inventors have found that by controlling the liquid density of the foamed dispersion, it is possible to achieve excellent control of the dissolution time, the dosage of active ingredient, as well as other properties of the suppositories.

Accordingly, it is an object of this invention to provide an intravaginal contraceptive device in the form of a suppository which is effective for at least about 2 hours, and which has a dissolution time of at least about 2 hours.

It is a further object of this invention to provide a contraceptive device in the form of a suppository which can be inserted intravaginally by the user, which maintains its position in the vagina for a prolonged period, including during intercourse, and which is completely and naturally soluble therein, thereby obviating the need for removal.

It is a further object of this invention to provide a method for manufacturing the intravaginal contraceptive device described herein, whereby the method provides for the production of suppositories having substantially equivalent densities, dissolution times, dosages, and softness and flexibility properties.

Further objects and advantages of the present invention will be made known in the following description of the preferred embodiments and claims.

DETAILED DESCRIPTION OF THE INVENTION

The contraceptive device of this invention comprises an intravaginally-dissolvable suppository comprising a water-soluble lyophilized foam and a contraceptive, wherein the suppository has a density of about 0.001 to about 0.1 gm/cc and a dissolution time of at least about 2 hours. The suppositories of the invention provide for the sustained and/or controlled release of a contraceptive wherein the contraceptive is effective for at least about 2 hours, and preferably for at least about 4 hours, after insertion into the vagina. The term "sustained release" means that the concentration of the contraceptive is maintained at a relatively constant level in the vagina. The term "controlled release" means that the contraceptive is administered over a period of time.

The term suppository, as referred to herein, means any solid substance, of any shape, which is intended to be inserted into the vagina. The suppository of the invention is intended to be inserted by the user and does not require fitting by a physician as, for example, in the case of an intrauterine device. It can be easily inserted digitally or with an applicator. Furthermore, it is completely and naturally soluble in the vagina.

The suppository is designed to be inserted into the vagina, preferably proximate to the cervix, prior to intercourse and maintained intravaginally for at least about 2 hours following intercourse. Upon insertion and contact with the moist mucous membrane (i.e., the lining) of the vagina, the suppository naturally and slowly begins to dissolve by fluid absorption. As the suppository dissolves, it continually releases an effective amount of contraceptive (typically a spermicide) into the vaginal area, in a dosage sufficient to substantially reduce the likelihood of pregnancy resulting from intercourse.

In one preferred embodiment of the invention which particularly facilitates intravaginal retention, the suppository is designed to adhere to the mucous membrane of the vaginal cavity. Upon contact with mucus which is excreted by the mucous membrane, the muco-adherent suppository hydrates, thus adhering the suppository to the membrane. This permits the device to be worn comfortably and prevents it from being expelled prematurely.

Accordingly, delivery of the contraceptive is not interrupted.

Upon dissolution, the lyophilized foam first forms a gel (i.e., a colloidal solution having the consistency of jelly), and then further dissolves into a liquid. The gel so formed possesses good structural integrity for a prolonged period prior to further dissolution to a liquid. For example, upon inspection at least 2 hours after the suppositories of the invention have been placed in aqueous solution at 37° C., a substantial amount of gel (at least about 10% by volume) still remains visible to the naked eye. This gelling feature prevents undesireable premature leakage; in addition, it promotes intravaginal retention and thus, greater effectiveness, of the contraceptive.

The time required for the suppositories of the invention to attain substantially complete in-vitro dissolution to a liquid, (i.e., no gel is evident), as measured by the method described below, is referred to as "dissolution time." By applying the teachings of this invention, dissolution times of at least about 2 hours can be obtained, preferably at least about 3.5 hours, more preferably at least about 8 hours, even more preferably at least about 20 hours, and most preferably at least about 24 hours. Moreover, in-vivo dissolution times are likely be even greater.

The procedure described in USP XXII, 711 DISSOLUTION, Apparatus 1, from U.S. Pharmacopeia was followed to determine the dissolution time. This procedure uses an assembly consisting of a covered glass vessel (a Bell jar), a motor, a drive shaft, a basket, and a constant temperature water bath. The speed regulating device used allows the shaft rotation to be selected and maintained at a rate of 35 rpm. The basket is affixed to the drive shaft. The vessel is filled with 200 ml of 1% (by weight) saline solution. The suppository is placed in a dry basket at the beginning of each test, and the basket is immersed in the vessel containing the saline solution. The vessel is then immersed in a constant temperature water bath set at 37° C. The sample is observed, and as dissolution takes place, the time for total gellation is recorded. The test is allowed to continue and the time for total dissolution of the gel is also recorded.

The dissolution time, density, and other physical characteristics of the suppository like flexibility and softness are due, in part, to the identity of the particular water-soluble polymer and contraceptive selected, their respective amounts, and the novel manufacturing process described herein.

The first step in producing the lyophilized foam suppository of the invention comprises forming an aqueous dispersion comprising at least one, and preferably several, water-soluble polymers, and a contraceptive. The term "aqueous dispersion" as used herein is meant to include dispersions (including solutions) in which the solvent is water and optionally, water-miscible liquids.

Preferably, the polymer is initially added to the solvent and dispersed, followed by addition and dispersion of the contraceptive. If necessary, heat can be applied to the mixture to facilitate dispersion.

Cellulose, cellulose ethers, derivatives thereof, and polymers of the type disclosed in U.S. Pat. No. 4,615,697, issued to Robinson, and commercially available under the generic name "polycarbophil" are suitable for use in the present invention. Other suitable polymers include polycarboxylated vinyl polymers, including polyacrylic acid polymers, polyacrylic acid polymers that are lightly crosslinked with a polyalkenyl polyether, such as those commercially available from B. Goodrich, Cincinnati, Ohio, under the trademarks, Carbopol® 434, 934P, 940 and 941, polysaccharide gums (such as natural plant exudates including e.g., karaya gum, ghatti gum and the like), and seed gums (including e.g., guar gum, locust bean gum, psigllium seed gum and the like). Cross-linked alginate gum gels of the type described in U.S. Pat. No. 3,640,741 to Etes are also suitable.

Preferably, the polymer is selected from the group consisting of polyurethanes, gelatins, celluloses and cellulose ethers, including hydroxypropylmethylcellulose, sodium carboxymethylcellulose, methylcellulose, hydroxyethylcellulose, hydroxypropylcellulose, hydroxyethylmethylcellulose, hydroxyethylethylcellulose, hydroxypropylethylcellulose, carbopol, polyvinyl alcohol and derivatives thereof, dextran, chitosan and its derivatives, starch and its derivatives, polyacrylamides, polyacrylates, agar, collagen, fibronectin, alginic acid, pectin, hyaluronic acid or mixtures thereof.

Foams comprised of cellulose ethers are especially preferred. In particular, it has been found that suppositories comprising hydroxypropylmethylcellulose, a mixture of gelatin and hydroxy-propylmethylcellulose or a mixture of hydroxypropylmethylcellulose and sodium carboxylmethylcellulose possess excellent qualities, including good adherent properties.

Certain polymers, such as cellulose ethers generally and hydroxypropylmethylcellulose in particular, may be employed to provide liquid foams having good stability and structural integrity, and dry foams with desirable softness. Other polymers, like gelatin, may be incorporated in the contraceptive devices of the invention to make them sufficiently rigid, so that the device can be inserted digitally or with an applicator without breaking or fracturing. One skilled in the art can readily determine the polymeric ingredients and their amounts that result in a device having the preferred combination of suitable properties.

Typically, polymer is added to the dispersion at a concentration of about 1% to 20% (by weight of the total dispersion including contraceptive), preferably about 2 to 16%, even more preferably about 2 to 7%. At lower concentrations, there may be insufficient polymer to prepare a sturdy foam, whereas at higher concentrations, the dispersion may be too viscous to foam under normal conditions.

The term contraceptive is meant to include any substance that tends or serves to prevent conception or impregnation in any animal, including but not limited to humans. Spermicides are preferred, especially nonoxynol-9. Additional spermicides that may be incorporated into the suppositories are described in U.S. Pat. No. 3,995,633 (Gougeon), which is incorporated herein by reference.

The contraceptive may be provided in the dispersion at a concentration of about 1% to about 25% (by weight of the total dispersion), with about 5% to about 15% being preferred. The contraceptive may be present at from about 20% to about 95% by weight of the (dry) suppository, with about 50% to about 80% by weight being preferred.

The amount of contraceptive incorporated into the suppository affects the in-vivo efficacy of the suppository, its tactile and structural properties, and the ease with which it may be manufactured. For example, suppositories containing relatively higher percentages of contraceptive may be more efficacious and more flexible; however, such suppositories may feel unpleasantly greasy to the user and have inadequate dissolution times. Suppositories having lower percentages of contraceptive may be too brittle; however, they may possess more desireable dissolution times. Accordingly, it is necessary to empirically determine the amount of active ingredient that results in a device having the preferred combination of suitable properties.

In practicing this invention, it has been determined that a suppository comprising a mixture of gelatin and hydroxypropylmethylcellulose in an initial ratio of 12:1 (by weight in the aqueous dispersion), and about 10–15% nonoxynol-9 (by weight in the aqueous dispersion) is preferred. Such a suppository is sufficiently soft, flexible, sturdy and mucoadherent.

The suppositories of the invention may further contain additional materials including, but not limited to, preservatives, fillers, excipients, binders, plasticizers, surfactants, wetting agents or penetration agents. Methyl paraben is a preferred preservative.

All materials incorporated into the suppository should be blended into a homogeneous mixture prior to foaming.

In order to ensure that the aqueous dispersion will subsequently foam, the viscosity of the dispersion should be maintained at about 4500 to 7000 cps, preferably about 5000 to 6000 cps, most preferably about 5600 cps, as measured on a Brookfield viscometer at 32° C. using a number 4 spindle at 20 rpm. Accordingly, it may be necessary to cool the dispersion, preferably to about 32 to 35° C., with mixing in order to maintain its viscosity.

After all materials to be incorporated into the suppository have been blended into an aqueous dispersion having adequate viscosity for foaming, the dispersion is then transferred to a continuous, enclosed mixer known as an "Oakes" foamer. An Oakes foamer is capable of operating under pressure to foam the dispersion and is typically used to manufacture creamy, smooth food products like ice cream and marshmallows. U.S. Pat. Nos. 2,572,049, 2,600,569, 2,679,866, and 3,081,069 describe various Oakes foamers useful for practicing the method of the invention, and the disclosures of these patents are incorporated herein by reference. The model referred to as the Oakes 2" Mixer, Model No. #2MT.5A is especially preferred for use in practicing the invention.

An Oakes foamer is comprised of an electrical system, an air system and a product section. Generally it comprises a pump; a mixing chamber; a head assembly having a rotor; a gas inlet; an outlet for the foamed dispersion; means to measure pump speed, rotor speed, flow rate and pressure of an incoming gas; and means to measure the back pressure of the foamed dispersion.

The electrical system consists of a main power switch, and two independently variable speed controllers and motors with digital tachometers to measure the rotor and pump speed.

The air system consists of a manual on/off toggle valve, pressure regulator and gauge, an adjustable flow valve and meter and a one way (check) valve.

The product section consists of a positive displacement pump; speed reducer; inlet piping; a back pressure gauge to monitor back pressure; and a mixing chamber. The gauge is isolated from the product by diaphragm seal assembly.

A liquid dispersion is fed to the pump, transmitted through a line to the mixing chamber wherein it is combined with air under pressure and mixed by the head assembly with rotor. In the mixing chamber, the dispersion is foamed, and the air and the dispersion are blended into a substantially uniform, homogeneous mixture. From the mixing chamber, the foamed dispersion is then sent to an outlet pipe.

It has been determined that the operating parameters of the mixer have a substantial effect upon the density of the liquid foam, and consequently, upon the properties of the suppositories produced. For example, increasing the pressure and/or flow rate of air into a fixed volume of dispersion generally produces a more flexible, faster dissolving suppository. Similarly, changing the pump speed or the rotor speed also changes the liquid density of the foamed liquid dispersion. The use of an enclosed foamer (like an Oakes foamer) permits each of these process variables to be separately monitored and independently altered in a controlled manner. Thus, it is possible to empirically determine the settings of the foamer which will produce a foamed dispersion having a desirable liquid density and, upon subsequent lyophilization, a suppository having suitable qualities. Moreover, the use of such a foamer makes it possible to accurately reproduce the settings so that a batch of suppositories having substantially identical properties, including dosages and dissolution times, is manufactured in each manufacturing sequence.

It has been found that the suppositories of the invention should have a (dry) density of about 0.001 to about 0.1 gm/cc, preferably about 0.001 to about 0.06 gm/cc, as determined using techniques which are well-known to those of ordinary skill in the art. A suppository with a density within these ranges possesses a good dissolution time. In addition, such suppositories are sufficiently sturdy, yet soft and flexible, so that the devices are comfortable to the user and yet do not readily break or fracture upon insertion.

Typically, in order to achieve suppositories with good physical characteristics, good dissolution times, and which are sufficiently efficacious at prolonged periods, foamer conditions are set as follows; pump speed about 25–30 rpm, air flow rate about 100–220 cc/min (at 100 psig input pressure), and rotor speed about 1000–2000 rpm. The foam that results generates a back pressure of about 10–40 psig during extrusion. Of course, the conditions are approximate since operational variability occurs in the meters during operation of the foamer. In addition, the dispersion probably has some air in it due to the dispersion formulation step. Prior degassing will likely alter the density of the solution and require a change in the liquid/air ratio in the foamer.

Any of these process variables can be changed, thereby changing the liquid density of the foam. In order to determine how the liquid density of the foam as well as the suppository produced from that foam are affected, foams can be manufactured using the Oakes foamer wherein only one process variable is varied and all other parameters remain constant.

For example, a series of foams of varying liquid density can be produced by varying the flow rate of the incoming gas. The liquid density of the resulting foam is determined using techniques that are well-known to those skilled in the art. A curve can be subsequently generated by plotting the density of the foamed liquid dispersion versus the flow rate.

The foamed dispersion produced from each run is then lyophilized (that is, freeze-dried under vacuum). Upon lyophilization, the suppository (whose foamed liquid density is known) is evaluated to determine whether it has certain desirable characteristics, including an adequate dissolution time. In this manner it is possible to empirically determine the liquid density of the foam which, upon lyophilization, results in a suppository having suitable properties. Accordingly, the setting necessary to foam the dispersion to the desired liquid density can be readily determined empirically or from the graph, and more importantly, controlled by the operator of the foamer who can easily reset the gas flow rate (or any other process variable) to the appropriate setting.

Therefore, by using the method of the invention one can substantially control the liquid density of the foamed dispersions, and ultimately, the physical properties including dosages, contraceptive delivery rates and dissolution times of the suppositories so produced.

Foaming can be continued until the back pressure gauge reaches an equilibrium value. Alternatively, one skilled in the art can readily determine when sufficient foaming has occurred by inspecting the viscosity of the foamed dispersion as it is extruded. Preferably, the density of the liquid foamed dispersion should range from about 0.1 to about 1.0 gm/cc. Liquid foam densities of about 0.4–0.6 gm/cc are even more preferred.

In the next step, the foamed liquid dispersion is placed into a receptacle having a known volume ("unit dosage"). Since the liquid density of the foam and the volume of the receptacle are known, it is a simple calculation to determine the foam weight and the amount of contraceptive incorporated into each unit dosage.

Accordingly, one skilled in the art can readily manufacture batches of devices containing known and substantially equivalent dosages of active ingredient.

Although the liquid can be cast into sheet form, it is preferably extruded through tygon tubing into a pre-formed mold. Various aluminum, plastic and release liner covered molds can be employed. Polyethylene molds are preferred, since the suppositories easily release from these molds without cohesive failure.

It is also preferred to extrude the foam into compartmentalized trays whereby the volume of one compartmental unit equals the volume of the resulting suppository. This prevents cold flow of the foam and thus, the manufacture of suppositories having nonuniform dimensions and dosages.

In another embodiment which favors contraceptive efficacy and wearing comfort, the mold may be constructed in the size and shape of a tampon.

The foamed dispersion is then lyophilized in a freeze drier in order to generate an open cell foam suppository which contains the contraceptive. A Virtis 800L-Freezemobile 12 is preferred. The freeze-drier shelves are chilled to below about −40° C. The condenser is chilled to below about −50° C. The filled molds are placed on the shelves and frozen to shelf temperature. The frozen foam is then exposed to the full vacuum (10–90 millitorrs) of the unit. Once this vacuum is achieved, the shelf temperature is gradually increased to about room temperature and sublimation continues for at least about 15 hours, or until the sample temperature reaches about 20°–25° C.

Thermal gravimetric analysis may be used to determine the water content of the foams. It may also be used to determine the thermal stability of the suppositories by determining degradative weight loss.

The contraceptive content of the suppositories may be determined by ultraviolet analysis of a solution of the dissolved foam.

The invention is further illustrated by the following examples which are not intended to be limiting.

EXAMPLES

Example 1

Preparation Of A Suppository Containing 10% Nonozynol-9 (by weight of the liquid formulation)
STEP 1. Dispersion Preparation Deionized water (833 g) was preheated to 200° F., and 2 g of methyl paraben was added with stirring. The solution was clear after about 5 minutes, and 5 g of hydroxypropylmethylcellulose (Methocel E4M) was added and dispersed. Then 60 g of 275 bloom gelatin was dissolved with stirring. The solution was then cooled. When the clear solution had cooled to about 35°–37° C., 100 g of nonoxynol-9 was added with stirring. The addition of the nonoxynol-9 caused the solution to become slightly turbid.
STEP 2. Foaming Procedure The solution of step 1, at about 31° C., was added to the hopper of an Oakes Foamer, (Model 2MT. 5A). The solution was pumped through the system at a speed of about 21 rpm. The initial 100–150 ml was purged and discarded. The remainder was recirculated. The mixer assembly was started, and the rotor was operated at 1053 rpm, until the viscosity had increased to a level sufficient to be foamed. Then air was added to the dispersion at an input pressure of 100 psig and a flow rate of 120 cc/min. The foam was generated at a back pressure of 38 psig, and extruded into nalgene tubes 1.25 cm in diameter and 6.0 cm in length.
STEP 3. Lyophilization Procedure The liquid foam samples were then placed on the shelves of a Virtis freeze drier (Unitop 800L with Freezemobile 12). These shelves were pre-chilled to −45° C. The condenser temperature was −65° C., and the sample temperature was −58 ° C. The frozen foam was lyophilized at full vacuum (90 millitorr) to a temperature of 15° C. The drying time was about 48 hours. The samples were then removed from the tubes manually.

Example 2

Preparation Of A Suppository Containing 5% Nonoxynol-9 (by weight of the liquid formulation)
STEP 1. Dispersion Preparation The solution was prepared as in Example 1 except that 50 g of nonoxynol-9 and 883 g of deionized water were formed into a dispersion.
STEP 2. Foaming Procedure The process in Example 1 was repeated with the following settings; pump speed 20 rpm, rotor speed 1082 rpm, air flow rate 70 cc/min and air pressure 100 psig. A back pressure of 10–12 psig was observed. The solution temperature at the time of addition to the foamer was 34° C.

STEP 3. Lyophilization Procedure

The lyophilization conditions set forth in Example 1 were repeated.

Example 3
Preparation Of A Lower Density Suppository Containing 10% Nonoxynol-9 (by weight of the liquid formulation)

STEP 1. Dispersion Preparation

The solution was prepared as in Example 1.

STEP 2. Foaming Procedure

The solution was foamed in the manner set forth in Example 1 at 32° C. The following settings were employed: pump speed 20 rpm, rotor speed 1075 rpm, air pressure 100 psig, and air flow rate 170 cc/min. A back pressure of 20–25 psig was observed. The liquid foam had a measured density of 0.555 gm/cc.

STEP 3. Lyophilization Procedure

The liquid foam was lyophilized under the conditions of example 1. The full vacuum was 15 millitorrs. Drying time was about 40 hours.

Example 4
Preparation Of A Higher Density Suppository Containing 5% Nonoxynol-9 (by weight of the liquid formulation)

STEP 1. Dispersion Preparation

The dispersion was prepared under the same conditions set forth in Example 1, using the following quantities of ingredients: 15 g of gelatin, 1.25 g of Methocel E4M, 0.5 g of methyl paraben (0.2%), 12.5 g of nonoxynol-9, and 221 g of deionized water.

STEP 2. Foaming Procedure

No foaming was employed.

STEP 3. Lyophilization Procedure

Conditions were the same as shown in Example 1.

Example 5
Preparation Of A Higher Density Suppository Containing 10% Nonoxynol-9 (by weight of the liquid formulation)

STEP 1. Dispersion Preparation

The dispersion was prepared as described in Example 4. The quantities of ingredients were also the same as set forth in Example 4, except that 25 g of nonoxynol-9 was added to 208 g of deionized water.

STEP 2. Foaming Procedure

No foaming was employed.

STEP 3. Lyophilization Procedure

The lyophilization conditions set forth in Example 4 were repeated.

Example 6
Preparation Of A Higher Density Suppository Containing 15% Nonoxynol-9 (by weight of the liquid formulation)

STEP 1. Dispersion Preparation

The dispersion was prepared as in Example 4. The quantities of ingredients were the same as Example 4 except that 37.5 g of nonoxynol-9 was added to 196 g of deionized water.

STEP 2. Foaming Procedure

No foaming was employed.

STEP 3. Lyophilization Procedure

Conditions of lyophilization were the same as Example 4.

Contraceptive Device Assay

A suppository was dissolved in water and analyzed by UV/VIS spectroscopy. A 147.2 ug/ml solution of the device exhibited UV absorbances at 225 nm and 275 nm due to nonoxynol-9, and another absorbance at 255 nm due to gelatin. The spectra of the placebo foam and nonoxynol-9 confirmed the wavelengths.

A curve-fitting program was used to determine the concentration of the contraceptive in the suppository. Thus, in one suppository the calculated dose of nonoxynol-9 was 69% by weight (of the dry suppository) while the experimentally-determined value was 65%.

Thermal Gravimetric Analysis

The suppositories were subjected to thermal gravimetric analysis (TGA) at a heating rate of 10° C./min to 400° C. The onset of weight loss due to water loss occurred between 50°–100° C., and was about 3–5% of the sample weight. Weight loss due to thermal degradation of a placebo suppository occurred at 256° C., while the nonoxynol-9 containing suppository did not exhibit weight loss until the temperature reached 291° C. This was apparently due to the presence of the nonoxynol-9 since its weight loss onset temperature was 321° C.

Effect Of The Density And The Contraceptive Content Of The Lyophilized Foam On Dissolution Time The dissolution time of the suppository may be changed by changing either the density of the lyophilized foam or the contraceptive content. For example, the dissolution time can be decreased by decreasing the density of the foam (i.e. increasing the air content of the foam) or increasing the content of contraceptive. This is depicted in Table I where suppositories containing 43% or 60% nonoxynol-9 (by weight of solids in the dry suppository) were prepared using the method described herein, except that some samples were made without air.

TABLE I

| Sample | Weight, g* | Dissolution Time |
|---|---|---|
| 1. 43% nonoxynol-9 foam/no air | 0.515 | >23 h |
| 2. 43% nonoxynol-9 foam/no air | 0.468 | >23 h |
| 3. 60% nonoxynol-9 foam/no air | 0.685 | <23 h |
| 4. 60% nonoxynol-9 foam/no air | 0.688 | <23 h |
| 5. 43% nonoxynol-9 foam/70 cc/min air | 0.368 | <23 h |
| 6. 43% nonoxynol-9 foam/70 cc/min air | 0.399 | <23 h |

*Each sample had the same constant volume.

Each of the samples gelled rapidly when placed in solution. After about 2 hours, about 35% of the gel of samples 1, 2, 3 and 4 remained, while about 25% of the gel of samples 5 and 6 was left. After about 3.5 hours, about 25% of the gel of samples 1, 2, 3 and 4 remained, while about 15% of the gel of samples 5 and 6 was left. After about 23 hours, samples 3, 4, 5 and 6 were completely dissolved, while about 5% of the gel remained from samples 1 and 2.

Accordingly, the suppositories of the invention possess excellent in-vitro dissolution times.

Effect Of Foam Density And Spermicide Content On The Flexibility Of The Suppository The flexibility of the suppository can be affected by the density and by the contraceptive content of the lyophilized foams. For example, tampon-shaped suppositories were tested in the horizontal position using an Instron machine. Procedure ASTM-D-780 was used except that the crosshead speed was 5 inches per minute, and the chart speed was 8 inches per minute. The tester was provided with a recorder adopted to provide a stress/strain curve. The force that was measured was the force required to cause failure in bending the suppository in the horizontal position using a 3-point load device. The two support prongs were spaced approximately one inch apart. The specimens to be tested were not conditioned. The test specimens were ½ inch in diameter and 2.2 inches long.

TABLE II

| Sample | Force, lbs |
| --- | --- |
| 60% nonoxynol-9 foam, no air | 4.90 |
| 43% nonoxynol-9 foam, no air | >5.00 |
| 60% nonoxynol-9 foam, 170 cc/min | 1.00 |
| 43% nonoxynol-9 foam, 70 cc/min | 3.35 |

As shown above, increasing the amount of contraceptive and/or decreasing the density of the foam resulted in a more flexible suppository.

IN-VIVO EFFICACY STUDIES

Primate mating studies were performed to determine the in-vivo efficacy of the suppositories. Suppositories containing either about 60% or 69% nonoxynol-9 (by weight in the lyophilized suppository) were placed in the vagina of a primate prior to mating. The results are set forth in Table III below. The "% motility" refers to the percentage of sperm that survive, and "forward progression" refers to the percentage of surviving sperm that move forward. The percentages of nonoxynol-9 indicate the percentage of spermicide (by weight) that was added to the aqueous dispersion prior to foaming.

TABLE III

Primate Mating Studies

Foam containing 10% Nonoxynol-9

| % Motility | % Forward Progression | Sperm Conc (×10⁶/ml) |
| --- | --- | --- |
| Zero Hour Single Mating | | |
| 0 | 0 | 48 |
| 0 | 0 | 117 |
| 0 | 0 | 54 |
| Six Hour Single Mating | | |
| 22 | 90 | 48 |
| 52 | 90 | 144 |
| 42 | 92 | 141 |

Foam containing 15% Nonoxynol-9

| % Motility | % Forward Progression | Sperm Conc (×10⁶/ml) |
| --- | --- | --- |
| Zero Hour Mating | | |
| 0 | 0 | 109 |
| 0 | 0 | 118 |
| 0 | 0 | 88 |
| Four Hour Mating | | |
| 0 | 0 | 127 |
| 0 | 0 | 212 |
| 0 | 0 | 376 |
| Eight Hour Mating | | |
| 0 | 0 | 85 |
| 0 | 0 | 347 |
| 25 | 50 | 215 |
| 0 | 0 | 99 |

TABLE III-continued

Primate Mating Studies

Foam containing 15% Nonoxynol-9

| % Motility | % Forward Progression | Sperm Conc (×10⁶/ml) |
| --- | --- | --- |
| Zero Hour Single Mating | | |
| 0 | 0 | 96 |
| 0 | 0 | 112 |
| 0 | 0 | 67 |
| 0 | 0 | 96 |
| 0 | 0 | 112 |
| 0 | 0 | 67 |
| 0 | 0 | 45 |
| 0 | 0 | 123 |
| 0 | 0 | 83 |

Zero hour single mating means that, upon insertion of the suppository, the primates immediately were permitted to commingle and mate once. Mating times of 4 or 6 hours means that, upon insertion of the suppository, the primates were not permitted to commingle until the indicated time period had passed.

As indicated above, all of the suppositories were extremely effective at zero hour single mating. In addition, suppositories containing 69% nonoxynol-9 remained effective even at prolonged mating times of 4 to 8 hours, whereas the suppository containing 60% of the contraceptive lost some of its effectiveness.

The efficacy tests described in Table III indicate that suppositories made from a dispersion containing a liquid concentration of about 15% nonoxynol-9 were most efficacious. The resulting suppositories were sufficiently flexible, however, they also tended to be greasy to the touch and dissolved too quickly. Suppositories made from a liquid dispersion containing about 10% nonoxynol-9 were sufficiently flexible and effective at zero hour single mating; but they were less effective at longer times. Suppositories made from a liquid dispersion containing about 5% nonoxynol-9 were not evaluated in-vivo, but were found to be brittle and dissolved even more slowly than the other samples.

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than by the foregoing description, and all changes which come within the meaning and range of equivalency of the claims are intended to be embraced therein.

What is claimed is:

1. A method of intravaginal contraception, comprising:
    (a) providing a water-soluble, muco-adhesive suppository comprising a solid soluble lyophilized foam and a contraceptive, said suppository having a density of about 0.001 to about 0.1 gm/cc and a dissolution time of at least about 2 hours;
    (b) inserting said suppository intravaginally prior to intercourse to adhere to the mucous membrane of the vagina;
    (c) maintaining said contraceptive intravaginally for a prolonged period following intercourse and prior to its natural intravaginal dissolution.

2. An intravaginally dissolvable contraceptive suppository comprising a water-soluble lyophilized foam and a contraceptive, said suppository having a density of about 0.001 to about 0.1 gm/cc and a dissolution time of at least about 2 hours, said foam comprising gelatin and hydroxypropylmethyl cellulose.

3. An intravaginally dissolvable contraceptive suppository comprising a water-soluble lyophilized foam and a contraceptive, said suppository having a density of about 0.001 to about 0.1 gm/cc and a dissolution time of at least about 2 hours, said foam consisting essentially of gelatin, hydroxypropylmethyl cellulose and nonoxynol-9.

4. An intravaginally dissolvable contraceptive suppository comprising a water-soluble lyophilized foam and a contraceptive, said suppository having a density of about 0.001 to about 0.1 gm/cc and a dissolution time of at least about 2 hours, said suppository being muco-adherent and adherent to the mucous membrane of the vagina.

* * * * *